United States Patent [19]

Simon

[11] Patent Number: 5,279,591
[45] Date of Patent: Jan. 18, 1994

[54] PROTECTOR FOR NEEDLE CATHETER

[76] Inventor: Alexander Z. Simon, 4460 Ammon Rd., South Euclid, Ohio 44143

[21] Appl. No.: 940,758

[22] Filed: Sep. 8, 1992

Related U.S. Application Data

[63] Continuation of Ser. No. 763,364, Sep. 20, 1991, which is a continuation-in-part of Ser. No. 552,934, Jul. 16, 1990, Pat. No. 5,051,109.

[51] Int. Cl.$^5$ .............................................. A61M 5/00
[52] U.S. Cl. ...................................... 604/263; 604/192
[58] Field of Search ............... 604/110, 162, 164, 167, 604/171, 192, 197, 198, 263

[56] References Cited

U.S. PATENT DOCUMENTS

| | | | |
|---|---|---|---|
| 3,134,380 | 5/1964 | Armao | 128/215 |
| 3,658,061 | 4/1972 | Hall | 128/214.4 |
| 4,329,989 | 5/1982 | Dallons et al. | 128/218 R |
| 4,468,223 | 8/1984 | Minagawa | 604/263 |
| 4,636,201 | 1/1987 | Ambrose et al. | 604/192 |
| 4,725,267 | 2/1988 | Vaillancourt | 604/192 |
| 4,735,618 | 4/1988 | Hagen | 604/192 |
| 4,762,516 | 8/1988 | Luther et al. | 604/164 |
| 4,775,369 | 10/1988 | Schwartz | 604/263 |
| 4,795,443 | 1/1989 | Permenter | 604/198 |
| 4,804,371 | 2/1989 | Vaillancourt | 604/198 |
| 4,834,718 | 5/1989 | McDonald | 604/195 |
| 4,850,977 | 7/1989 | Bayless | 604/198 |
| 4,863,434 | 9/1989 | Bayless | 604/263 |
| 4,863,435 | 9/1989 | Sturman | 604/198 |
| 4,892,521 | 1/1990 | Laico | 604/192 |
| 4,929,241 | 5/1990 | Kulli | 604/263 |
| 4,955,866 | 9/1990 | Corey | 604/192 |
| 4,964,854 | 10/1990 | Luther | 604/263 |
| 4,978,344 | 12/1990 | Dombrowski | 604/198 |
| 5,013,305 | 5/1991 | Opie et al. | 604/192 |
| 5,051,109 | 9/1991 | Simon | 604/263 |

OTHER PUBLICATIONS

International Publication WO89/10767, Nov. 1989.
International Publication WO90/00075, Jan., 1990.

Primary Examiner—C. Fred Rosenbaum
Assistant Examiner—Manuel Mendez
Attorney, Agent, or Firm—Body, Vickers & Daniels

[57] ABSTRACT

A protector guard housing is disclosed for a catheter type needle apparatus to prevent accidental needle puncture. The guard housing is initially positioned between the hub of the catheter and the handle of the needle which slidably extends through the catheter in a known manner. A detent mechanism initially retains the forward end of the guard to the catheter hub while needle supports within the guard permits the needle to axially move relative to the guard. When the needle is withdrawn from the catheter after site puncture, a resilient closure wall formed in the protector closes the protector's forward end while the needle's cutting end is simultaneously wedged into contact with friction retention material in the protector. The needle's cutting end is thus encapsulated within the protector when the detent mechanism releases the protector from the catheter.

32 Claims, 2 Drawing Sheets

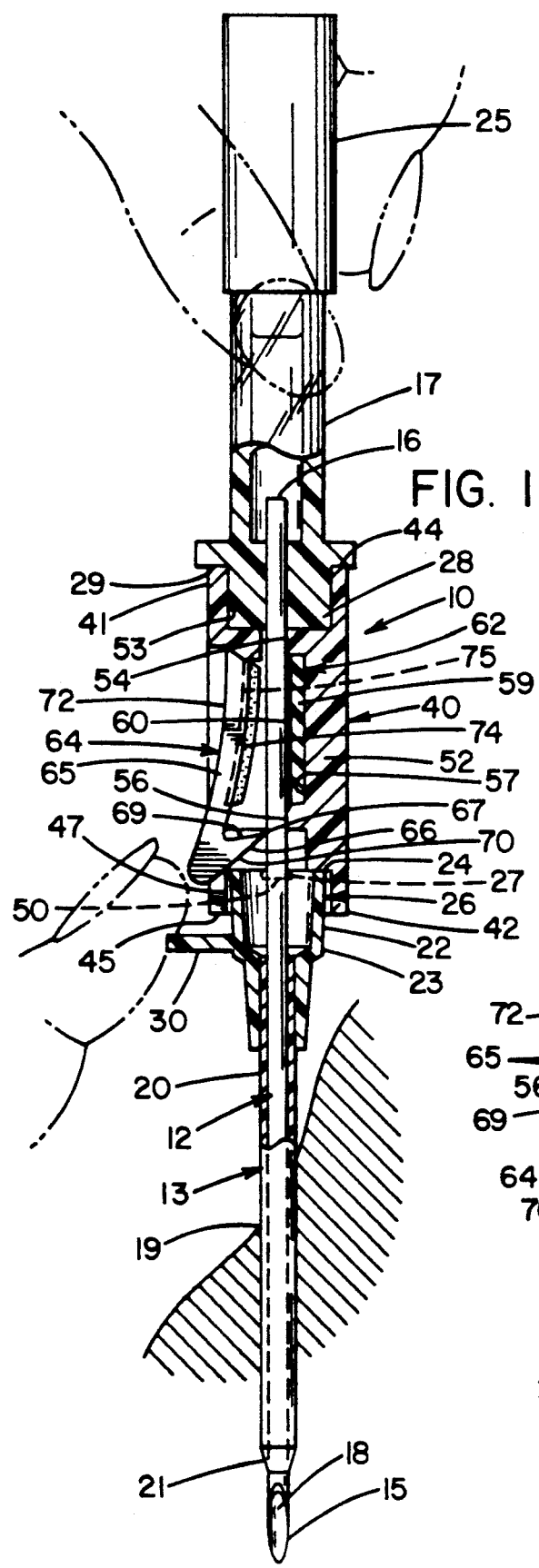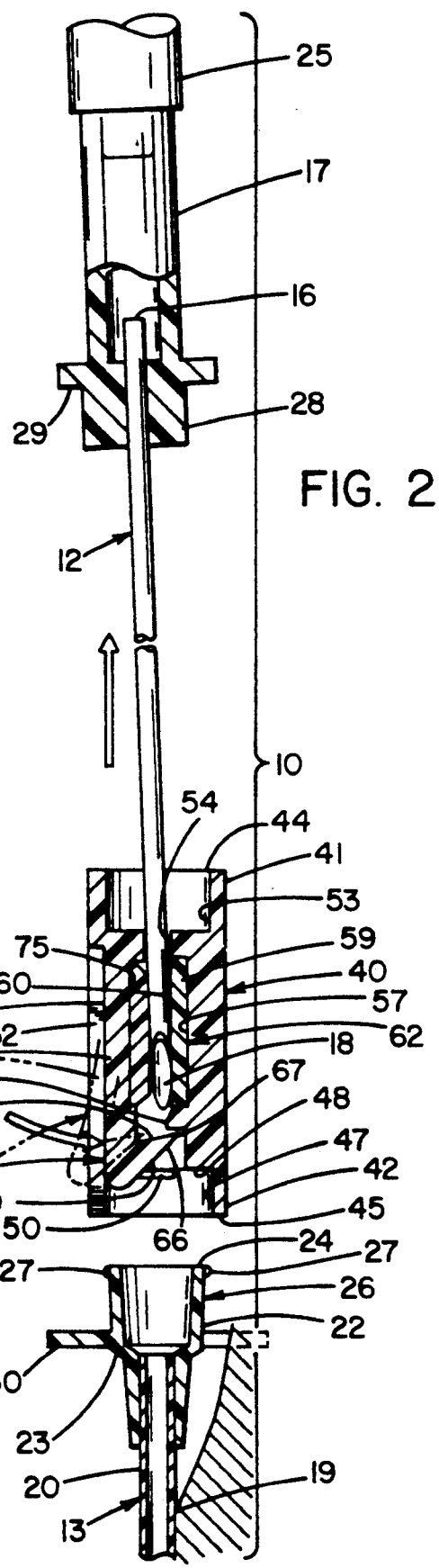

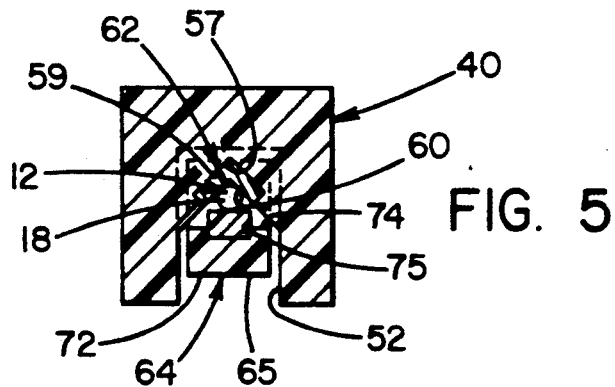
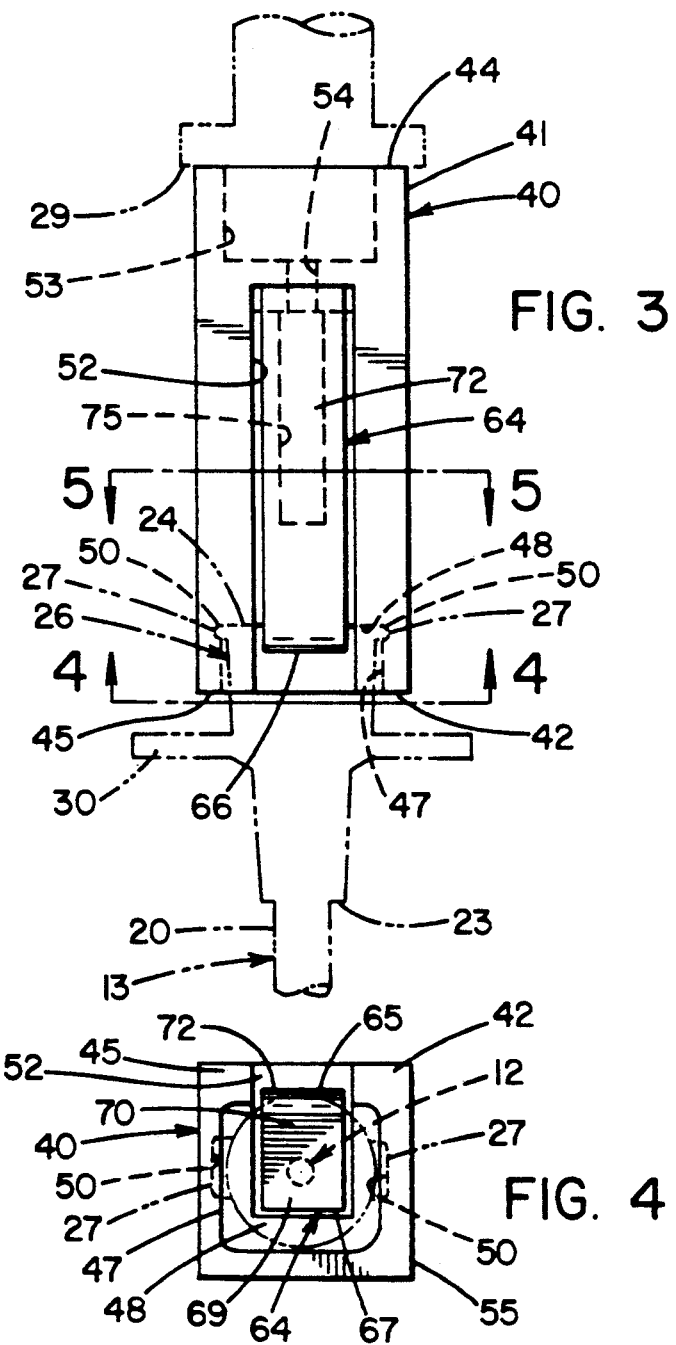

PROTECTOR FOR NEEDLE CATHETER

This is a continuation of Ser. No. 763,364, filed Sep. 20, 1991, which is a continuation-in-part of my prior application, Ser. No. 552,934 filed Jul. 16, 1990 now U.S. Pat. No. 5,051,109.

This invention relates generally to an improvement in medical needles of the catheter type and more particularly to a protective device for preventing accidental needle puncture after use.

INCORPORATION BY REFERENCE

My prior application Ser. No. 552,934 filed Jul. 16, 1990, now U.S. Pat. No. 5,051,109, including its drawings is incorporated herein by reference in its entirety and made a part hereof. In addition Luther et al U.S. Pat. No. 4,762,516 dated Aug. 9, 1988; McDonald U.S. Pat. No. 4,834,718 dated May 30, 1989 and Corey U.S. Pat. No. 4,955,866 dated Sep. 11, 1990 are incorporated herein by reference so that the specifications hereof need not define in detail conventional material known in the prior art.

BACKGROUND OF THE INVENTION

The concern over acquired immune deficiency syndrome (AIDS) and other infectious diseases such as hepatitis has resulted in a number of protective devices designed to prevent accidental puncture to clinical personnel after use of a medical needle. Most of the protective devices have been developed for hypodermic needles as opposed to needles of the type to which the present invention relates. Medical apparatus employing needles of the type to which the present invention relates typically comprise a hollow inner needle which has a cutting or pointed edge for puncture and a concentric cylindrical device which slidingly receives the hollow needle. Typically, the outer cylindrical device is a catheter although the outer device could be the outer cannula of a biopsy needle. In needles of this type, the puncture is made with one hand similar to that of a hypodermic needle, but the withdrawal of the needle from the puncture site is made with two hands thus raising the likelihood of accidental needle puncture resulting from clinical personnel holding the catheter in a precise position while the needle is withdrawn.

The prior art has recognized the difficulties associated with catheters and has developed fail safe, puncture-proof devices as disclosed in the '516 and '718 patents incorporated by reference herein. Basically, the prior art devices modify the needle so that the needle is encased in a telescoping tubular arrangement. The needle conventionally punctures the patient's skin in a non-telescoped position. To withdraw the needle after puncture, the clinician grabs one end of the device while retracting the handle portion to telescope the handle so that the needle when withdrawn is retained within the expanded handle.

The prior art devices are effective but have not achieved wide scale commercial success principally because the cost of constructing a long, two-piece telescoping handle arrangement, even with relatively inexpensive plastics, materially increases the cost of the device compared to conventional, unshielded catheter needles. In addition, the prior art protective needles are more cumbersome to operate which may or may not be overcome with familiarity. Basically, the clinician prefers to advance the catheter with one hand while the needle is withdrawn with the other hand. In the prior art devices, the clinician must hold the telescoping barrel, sometimes by special or awkwardly placed tabs on the barrel. Although the barrel is fitted to the catheter hub, the point is that the attention of the clinician is focused away from the catheter while the needle is removed and the hand position is somewhat awkward. This can present problems in emergency situations, typically outside the confines of the hospital, where the catheter must be administered quickly.

To some extent the difficulties of the prior art described above are overcome somewhat by Corey '866 who discloses a removable protection guard for encapsulating the cutting edge of the needle after injection. However, Corey's protector guard is not easily removed from the catheter and does not positively lock the needle into the guard with the result that the device, in some instances, can be likely to cause an accidental puncture. Again, the clinician is familiar with utilizing a standard catheter and his attention is riveted onto making the injection and holding the needle in place while the catheter is advanced. Any protective device requiring some additional motion to actuate it or requiring attention to be directed away from the act of inserting and removing the needle is unsatisfactory.

THE INVENTION OF THE PARENT APPLICATION

In accordance with the invention disclosed in my parent application, Ser. No. 552,934 a conventional needle and a conventional catheter is provided with a guard housing having an open ended cylindrical base portion receiving the hub portion of the catheter in an initial position of the device and slidingly removable from the catheter when the needle is withdrawn. The guard housing has a closable front wall having an initial position whereat the front wall is removed from the base portion when the guard housing is positioned on the hub portion and a closed position where the front wall is positioned over one end of the base portion. The guard housing has a side wall contiguous with the base portion biasing the front wall to its closed position. A tether is affixed at one end to the guard housing and at its other end to the needle handle and is of a length sufficient to permit the needle end to be withdrawn from the catheter hub but insufficient to prevent the needle end from being withdrawn from the open end of the base portion of the guard whereby the needle end is maintained within the guard housing to prevent inadvertent puncture therefrom.

In accordance with a more specific feature of the parent invention, the protector guard housing has an open ended, cylindrical base portion concentric with the catheter's hub portion and contiguously extending from the rearward end of the guard housing toward the forward end. The cylindrical base portion has diametrically opposed, radially outwardly extending notches formed therein and the catheter hub portion has diametrically opposed, radially extending locking ears so that the ears are received within the notches of the base portion when the guard housing is initially positioned on the catheter hub to permit the guard housing to slide off the hub and the cylindrical base to receive the needle when the needle is withdrawn from the catheter. The guard housing has a resilient side wall portion contiguous with its rearward end and also with the forward end and the side wall is displaced radially outwardly from the guard's base portion. The guard's forward end is defined by a sealable front wall portion which is contiguous with the side wall and the front wall covers at least a portion of the cylindrical opening at the forward end of the cylindrical base portion when the guard housing slides off the catheter base to prevent puncture by the needle's cutting edge. The front wall is displaced radially outwardly by contact with the catheter's hub portion in the initial position whereat the base portion slidingly engages the catheter hub so that the side wall is effective to resiliently bias the front wall to its closed position while simultaneously and to a lesser extent biasing the base portion into contact with the catheter's hub portion thereby insuring a sliding engagement between the guard housing and the catheter hub so that the guard is not inadvertently pulled from the hub prematurely. The side wall is preferably discontinuous and extends circumferentially about the catheter's hub portion a distance which subdivides an arc of at least about 90° and two diametrically opposed side wall segments may be provided with each containing a front wall segment which can interlock with one another when snapped to their closed position.

In accordance with another aspect of the parent invention, the tether may simply comprise a cord of a length equal to the length of the intermediate portion of the needle and the length of the base portion of the guard must be at least equal to the diameter of the base portion to prevent dislodgement of the needle from the base portion. Optionally, the cord can be provided with an elastic portion to bias the cutting edge of the needle into contact with the front wall after needle removal. Alternatively, the tether can comprise an integral, relatively wide plastic ribbon which is formed as part of the guard housing in the shape of a single coil which is unwound when the needle is withdrawn from the catheter to maintain the guard housing affixed to the hug and assist in withdrawing the needle from the catheter.

SUMMARY OF THE INVENTION

Accordingly, it is a principle object of the invention to provide a fail safe protector for needle apparatus for administering catheters and the like which overcomes the prior art disadvantages discussed above.

This object along with other features of the invention is achieved in a medical needle apparatus of the catheter or biopsy type which prevents accidental punctures. The needle apparatus includes a needle having a cutting edge at its proximal end for effecting a puncture, a handle portion at its distal end and a cylindrical body portion between its ends, and a catheter (or a cannula) having a proximal forward end initially adjacent the needle's cutting edge, a hub portion at its distal end and a generally cylindrical body portion therebetween so that the catheter slidably receives the needle's body portion. A hollow protector guard housing is positioned in between the catheter's hub portion and the needle's handle portion and slidably receives the needle's body portion. The guard housing has an open forward end initially engaged with the catheter's hub portion and a rearward end with a rearward opening initially adjacent the needle's handle portion. A resilient spring arrangement within the guard housing is actuated upon movement of the cutting edge of the needle out of the catheter to close the forward end opening of the guard housing. A friction retention arrangement within the guard housing is effective upon actuation of the spring arrangement to frictionally engage the needle and retain the needles cutting edge within the guard housing thereby preventing inadvertent puncture from the needle after use.

In accordance with another aspect of the invention a detent arrangement is provided between the hub portion of the catheter and the forward end of the guard housing for initially maintaining the guard housing connected to the catheter's hub portion while permitting separation of the guard housing from the hub portion after actuation of the spring arrangement upon withdrawal of the needle from the catheter. More specifically, the catheter's hub portion preferably has diametrically opposed, radially-outwardly extending, conventionally standard catheter locking ears and the forward end of the guard housing has a recessed notch formed therein for receiving the ears whereby the hub portion is initially engaged with the guard housing while the ears are pulled from the recess to separate the guard housing from the hub portion of the catheter upon needle withdrawal. In accordance with a still further aspect of the invention, the resilient spring arrangement can also function to separate catheter hub from the guard housing.

In accordance with another specific object of the invention the guard housing has a hollow body portion extending between its forward end and its rearward ends and the body portion includes a resilient sidewall segment formed therein extending from the forward end towards the rearward end. The sidewall segment includes a closure wall terminating at a contact edge surface adjacent the guard housing's forward open end and sized to substantially cover the guard housing's forward open end. The closure wall's contact edge surface is in contact with the needle's body portion when the needle is within the catheter to resiliently bias the sidewall segment outwardly from the guard housing body portion whereby the sidewall segment resiliently snaps the closure wall over the guard housing's open forward end when the needle's cutting edge is moved out of the catheter and past the closure wall thus insuring a positive, snap action closure of the guard housing.

In accordance with another specific aspect of the invention the rearward end of the guard housing defines a rearward needle support surface and the guard housing's body portion has an inwardly-extending forward needle support surface adjacent the guard housing's forward end and positioned away from and between the rearward needle support surface and the closure wall of the sidewall segment whereby the body portion of the needle is slidably engaged with the rearward needle support surface, the forward needle support surface and the closure wall's contact edge surface. The guard housing's body portion is recessed between the forward needle support surface and the rearward needle support surface and a friction material is disposed within the recess. The friction material has an exposed surface adjacent or facing the needle's body portion and the exposed surface is positioned inwardly within the guard housing body portion a distance less than the forward and rearward needle support surfaces whereby the needle's body portion becomes frictionally wedged against the exposed surfaces only when the needles cutting edge is moved out of the catheter and past the needle forward support surface. Alternatively, the friction material could be applied only to the sidewall segment or to both sidewall segment and recess.

It is thus an object of the present invention to provide a guard housing for needle apparatus which prevents accidental puncture from the cutting end of the needle after use.

It is another object of the invention to provide a protector for a medical needle to prevent puncture from the cutting end of a needle which is simple and economical.

Yet another object of the invention is to provide a guard for preventing inadvertent puncture by a catheter needle apparatus which can be applied to existing designs of needle catheters.

Yet another object of the invention is to provide a guard to prevent inadvertent puncture after use from a needle catheter apparatus which can be inserted and withdrawn from the patient with the same motion and same hand position as that currently used in conventional catheter needle apparatus.

Yet another object of the invention is to provide a plastic protector guard for catheter needle type apparatus which retains its resilient closure action not withstanding storage of the needle over long periods of time or storage of the needle in warm environments.

Still yet another object of the invention is to provide, an inexpensive, easily manufactured guard protector housing which can be applied to standard type catheter needles with the only modification being the requirement for a slightly longer needle for preventing accidental puncture from the needle.

It is still another object of the invention to provide a tetherless guard protector housing for a medical, catheter type needle which simply snaps off the hub portion of the catheter upon needle removal while safely retaining the cutting edge of the needle therein.

It is still yet another object of the invention to provide a guard protector housing for medical needles of the biopsy type in which an inner cutting cannula is retained within an outer cannula.

These and other objects of the present invention will become apparent to those skilled in the art upon reading and understanding the detailed description of the invention as set forth in the section below.

BRIEF DESCRIPTION OF THE DRAWINGS

The invention may take form in certain parts and arrangement of parts, a preferred embodiment of which will be described in detail and illustrated in the accompanying drawings which form a part hereof and wherein:

FIG. 1 is a longitudinal, partially sectioned view of the needle of the present invention shown in its initial, applied position;

FIG. 2 is a partially sectioned, longitudinal view of the needle of the present invention similar to FIG. 1 but showing the needle after it has been used and is in its retracted position;

FIG. 3 is an elevational view of the guard protector housing;

FIG. 4 is an end view of the forward end of guard protector housing shown in FIG. 3; and FIG. 5 is a sectioned end view of the guard protector taken along lines 5—5 of FIG. 3.

DETAILED DESCRIPTION OF THE PREFERRED EMBODIMENT

Referring now to the drawings wherein the showings are for the purpose of illustrating a preferred embodiment of the invention only and not for the purpose of limiting the same, there is shown in FIGS. 1 and 2 an intravenous needle-catheter assembly generally designated by reference numeral 10 which basically includes a needle 12 and a catheter 13.

Needle 12 is hollow and has a cutting end 15 which could be simply a sharp pointed end, a rearward end 16 which is encased or embedded in a plastic handle 17 and an intermediate hollow tubular portion 18 in between cutting end 15 and rearward end 16. Needle 12 is used to effect tissue puncture at a site 19 in a conventional manner, for backdrawing blood through needle 12 and for the purpose of inserting catheter 13 into the site such as at a vein. For backdrawing of blood, handle 17 is shown as hollow and includes a removable, end cap 14. Needle 12 is typically made of a steel alloy.

Catheter 13 is plastic and flexible and in the preferred embodiment is conventional. Catheter 13 may be viewed as a cylindrical member concentric with needle 12 and slidingly receiving needle 12 therein and has a flexible, cylindrically hollow portion 20 with a forward edge 21 adjacent needle cutting edge 15 and a hub portion 22 at its rearward end. Actually, hub portion 22 and cylindrical portion 20 are separate plastic pieces which are press fitted together but will be referred to as portions of catheter 13 herein for terminology purposes. For definitional purposes, hub portion 22 has a forward end 23 and a rearward end 24. At rearward end 24 on the outside surface of hub portion 22 is a conventional catheter fitting 26 which remains outside the patient's body and is used for connecting a source for intravenous fluids and/or medication to the catheter. Catheter fitting 26 is conventionally referred to as a luer-type locking fitting and will be referred to herein as a pair of diametrically opposed radially extending ears 27 protruding from the outside surface of hub portion 22- at rearward end 24 thereof.

Needle handle 17 has a boss 28 which extends from shoulder 29 with rearward end 16 of needle 12 embedded within boss 28 as shown. Preferably boss 28 has a cylindrical outer surface defined by an outside diameter which approximates the inside diameter of hub portion 22 and in conjunction with the shape of a guard protector housing 40 of the present invention provides a rigid connection between catheter 13 and needle 12 for catheter insertion at the puncture site, etc. However, it should be apparent that boss 28 could be rectangular.

Adjacent forward edge 21 of hub portion 22 is a finger-tape support tab 30 which is only partially shown in the drawings. Tab 30 extends radially outwardly from hub portion 22 and circumscribes hub portion 22 through an included angle which does not exceed 180° whereat tab 30 stops. Tab 30 allows catheter 13 to lie flat against the patient's skin while tab 30 also permits strips of tape to be wrapped around the tab for taping catheter 13 in place at the site. Additionally, tab 30 permits holding or moving catheter 13. As known to the clinician, needle 12 is withdrawn by relative movement between needle 12 and catheter 13. Typically needle 12 is held in a fixed position relative to the patient or site while catheter 13 is advanced to the vein. Tab 30 is utilized for this purpose. Importantly, the clinician does not hold the protector guard housing while extracting needle 12. Catheter 13 and needle 12, as thus far described, are entirely conventional and commercially available.

The invention includes an elongated, longitudinally extending, hollow, protector guard housing 40. Protector guard housing 40 has a rearward end 41 and a forward end 42. In the initial, as supplied position of needle catheter assembly 10 as shown in FIG. 1, rearward end 41 is adjacent annular shoulder 29 of needle handle 17 and forward end 42 is adjacent rearward end 24 of hub portion 22 of catheter 13. More specifically, rearward end 41 includes a longitudinally extending rearward annular shoulder 44 which in the "as supplied" or initial position of catheter assembly 10 receive boss 28 of needle handle 17 and the axial edge surface of rearward annular shoulder 44 is adapted to contact shoulder 29 of handle 17. Again, should boss 28 be rectangular, then shoulder 44 would be rectangular. Somewhat similarly, forward end 42 has a forward longitudinally extending shoulder 45 from guard housing 40 which receives rearward end 24 of hub portion 22 of catheter 13. Shoulders 44, 45 insure that guard housing 40 acts as a rigid connection of catheter 13 and handle 17 so that needle assembly 10 can be rigidly inserted at the puncture site.

Forward shoulder 45 is defined in part by an inner surface 47 which is perpendicular to a radially-inwardly extending surface 48. In the preferred embodiment, inner surface 47 is rectangular and radially-inwardly extending surface 48 is likewise rectangular and has a dimension which is sufficient to contact the circular edge of catheter hub rearward end 24. However, both inner surface 47 and radially-inwardly extending surface 48 could be circular in configuration. Formed within inner surface 47 is a pair of recesses or notches 50 which are 180° opposed to one another. If inner surface 47 was circular, notches 50 would simply comprise an annular groove. However, in the preferred embodiment, guard housing 40 is rectilinear and inner surface 47 is in the shape of the sides of a rectangle.

In the initial position of needle assembly 10 shown in FIG. 1, catheter hub ears 27 fit within notches 50 and retain hub 22 to guard housing 40. As noted above, catheter 13 is made of a flexible plastic material and the outer portions of ears 27 are flexible to some degree. Thus, the force which retains hub portion 22 connected to guard housing 40 is a function of the distance spanned by inner surface 47 (i.e. the diameter if inner surface 47 is circular in configuration) and the depth of notches 50. By controlling or sizing this dimensional relationship, the retention force between hub portion 22 and guard housing 40 can be precisely determined to permit separation of hub portion 22 from guard housing 40 in the manner as hereinafter described. It should also be noted that forward shoulder 45 in combination with notches 50 could be slitted and that inner surface 47 could be chamferred so that once ears 27 were pulled from notches 50, hub portion 22 would be instantly disengaged from guard housing 40. It is also within the scope of the present invention that hub portion 22 could be modified (not shown) so that its rearward end 24 extended beyond ears 27 such that ears 27 would be positioned in FIG. 1 to be outside of guard housing 40. The extension formed on hub portion 22 which would fit within guard forward shoulder 45 would then have a bead or a pair of beads radially extending outwardly which would snap into notches 50 and function as a spring biased detent mechanism.

Guard housing 40 includes a hollow body portion 52 extending between its rearward and forward ends 41, 42 which in the preferred embodiment is rectangular in configuration although such configuration could be cylindrical. Rearward end 41 has a rearward opening 53 formed about a rearward needle support 54 through which needle tubular portion 18 extends and rests thereon. Body portion 52 also has an inwardly-extending, forward needle support 56 upon which tubular needle portion 18 likewise rests on when needle 12 is within catheter 13.

Between rearward and forward needle supports 54, 56, body portion 52 is recessed as indicated by reference numeral 57. Within recess 57 there is positioned friction generating material 59 which has an inward, exposed surface 60 which extends inwardly into body portion 52 a distance less than that distance which rearward and forward needle supports 54, 56 extend and faces needle tubular portion 18. This feature of the invention permits needle 12 to axially move within protector guard 40 until needle cutting end 15 passes forward needle support 56 at which point the needle is trapped by or engaged with friction material 59. If friction material 59 extended radially inwardly beyond forward and rearward needle supports 56, 54, it would be in contact with needle 12 and resist any relative movement between catheter 13 and needle 12. This would not be desirable and could cause premature separation of catheter hub portion 22 from guard housing 40.

Friction material 59 could be a butyl rubber or a polyurethane compounded to have a relatively soft hardness to generate high friction. Other elastomers which can be utilized will suggest themselves to those skilled in the art. However, it is within the scope of the present invention that friction material 59 could in fact comprise the same plastic material used in guard housing 40 so long as appropriate provisions were made in the shape of inward exposed surface 60 of friction material 59. (Further, depending upon the type of plastic used, it is possible to have a flat inward exposed surface 60.) In the preferred embodiment, inward exposed surface 60 is formed as in the shape of a "V" 62 as best shown in FIG. 5. Alternatively, depending upon the type of friction material 59, inward exposed surface 60 would be simply constructed as a flat surface or alternatively, inward exposed surface 60 could be constructed to be corrugated such as in the shape of a sawtooth configuration. Further, the sawteeth could be formed as barbs canted or pointed towards forward needle support surface 56 and, in conjunction therewith, the depth at which recess 57 is filled with friction material 59 can be controlled so that the depth of exposed surface 60 gradually approaches the height of rearward needle support 54 as inward exposed surface 60 extends from forward support 56 to rearward support 54. In other words there would be a drop in the depth of friction material 59 adjacent forward support 56 and this drop in combination with a barbed tooth configuration would act to wedge and retain needle cutting end 15 into friction material 59. All such variations in friction material 59 and in the configuration of inward exposed surface 60 are within the scope of the present invention as disclosed herein.

Body portion 52 of guard housing 40 also has a resilient sidewall segment 64 formed as a part thereof. Sidewall segment 64 extends from forward end 42 of guard housing 40 toward rearward end 41 where it is contiguous with body portion 52. Sidewall segment 64 has a longitudinally extending portion 65 which extends from rearward end 41 towards forward end 42 and terminates at a closure wall portion 66 which extends inwardly therefrom and closure wall portion 66, in turn, terminates at a contact edge surface 67. In the preferred embodiment closure wall portion 66 has a rearward surface 69 generally perpendicular to longitudinally extending portion 65 and a tapered forward surface 70 so that contact edge surface 67 assumes a narrow width.

Importantly tapered forward surface 70 functions in the preferred embodiment as a camming surface when resilient sidewall segment 64 snaps from its FIG. 1 to its FIG. 2 position to contact rearward end 24 of catheter hub 22 and separate or assist in the separation of catheter 13 from guard housing 40. Longitudinally extending portion 65 has an outer surface 72 somewhat coplanar with the outer surface of body portion 52 and an inner surface 74 facing needle tubular portion 18.

Inner surface 74 may be relieved as indicated by reference numeral 75 adjacent rearward end 41 to better permit longitudinally extending portion 65 to assume a resilient, arcuate shape configuration when sidewall segment 64 is biased outwardly in the position shown in FIG. 1. It is specifically contemplated that the thickness of longitudinally extending portion 65 can be varied along its length to establish a predetermined spring force of sidewall segment 64 and also to establish a "normal" or perpendicular force against needle 12 when sidewall segment 64 is snapped into its closed position shown in FIG. 2 which is somewhat constant along the length of needle 12 within guard housing 14. Other configurations of sidewall segment 64 are possible. For example sidewall segment 64 could be shaped in the general configuration illustrated in FIG. 7 of my parent application Ser. No. 552,934 to increase its snap action effect. However, the configuration of longitudinally extending portion 65 as shown in the drawings hereof is believed to provide an adequate resilient force for working of the invention.

While it is preferred that the resilient spring mechanism employed in protector guard housing 40 comprise a resilient sidewall segment 64, it is within the scope of my invention that the resilient spring mechanism can be effected by external springs applied to a lever arm which has a forward end similar to forward end 42. That is those skilled in the art will recognize that sidewall segment 64 can be functionally replaced by a pivotable lever arm which is externally biased by any conventional spring arrangement. Such alternatives are specifically contemplated to come within the scope of my invention.

Further it should be noted that friction material 59 can be and is shown as applied to inner surface 74. It should be clear that it is within the scope of the invention to use friction material only in recess 57 or only on inner surface 74 or in both recess 57 and on inner surface 74 as shown. An important underlying concept of the invention is that the shape of sidewall segment 64 in combination with forward and rearward supports 56, 54 permits needle-catheter movement with the guard housing mechanism unactuated until needle position passes a predetermined point whereat the guard housing mechanism is actuated to trap the needle by frictional force engagement while optionally also separating catheter from the guard housing. A number of variations in design of the spring mechanism and the friction mechanism are possible consistent with the underlying concept. The embodiment disclosed is preferred because the embodiment has unique advantages over other arrangements. However, it is within the scope of the invention to include variations in design which achieve the underlying concept.

The operation of the invention is believed apparent from the discussion above. In the initial, "ready to use" position of needle assembly 10 shown in FIG. 1, needle 12 extends through protective guard housing 40 and resilient sidewall segment 64 is biased outwardly so that within body portion 52 needle tubular portion 18 rests on rearward and forward needle supports 54, 56 and contact edge surface 67 contacts needle tubular portion 18 diametrically opposite to the contact points provided by rearward and forward needle supports 54, 56. The puncture is made with needle assembly 10 in a conventional manner. The clinician then with the fingers of one hand holding tab 30 and the fingers of the other hand gripping needle handle 17 begins to relatively move needle 12 from catheter 13 in the ordinary, conventional manner to cause needle 12 withdrawal. There is some frictional force established between rearward and forward needle support surfaces 54, 56 and contact edge surface 67 which tends to resist movement of needle tubular portion 18 from protector guard housing 40. This force, however, is not significant and such force does not exceed the retention force between catheter hub portion 22 and notches 50 at guard housing forward end 42. Thus, it is not necessary for the clinician to hold body portion 52 or otherwise try to grip catheter 13 and guard housing 40. As needle 12 is withdrawn from catheter 13, needle cutting end 15 passes contact edge surface 67 whereupon resilient sidewall segment 64 snaps into the closed position shown in FIG. 2 and in this position, closure wall portion 66 closes forward end 42 of guard housing 40. At the same time, inner surface 74 of longitudinally extending portion 65 of sidewall segment 64 is snapped into contact with needle tubular portion 18. Also, at the same time, tapered forward surface 70 contacts rearward end 24 of catheter hub 22 to separate catheter 13 from guard protector 40. (The latter feature is optional because the invention will work without camming forward surface into contact upon relative needle movement.) When needle cutting end 15 passes forward needle support surface 56, sidewall segment 64 forces tubular needle portion 18 into contact with friction material 59. At this position needle tubular portion 18 is firmly clamped between inner surface 74 of resilient sidewall segment 64 and friction material 59. The length of recess 57 has been predetermined to establish a high frictional force, so that further retraction or rearward movement of needle 12 snaps or disengages catheter hub portion 22 from protective guard housing 40 should forward surface 70 not be used to disengage the catheter. Cutting end 15 of needle 12 is firmly retained within protective guard housing 40 which is closed at forward and rearward ends 41, 42 to prevent any accidental puncture to the clinician from needle cutting end 15. No special motion or actuation is required.

The invention has been described with reference to a preferred embodiment. Obviously, modification and alterations will occur to those skilled in the art upon reading and understanding a description of the invention disclosed herein. For example, the invention has been described with reference to an intravenous catheter needle apparatus. Such apparatus can be characterized generally as an inner cylinder concentrically disposed within an outer cylinder with one of the cylinders having at least a cutting end. This feature is shared with biopsy needles particularly with those biopsy needles which leave one of the cannulas at the puncher site. Thus, the invention is particularly suited for application to such biopsy needles as well as to the I.V. catheter needle application disclosed herein because guard housing 40 will protect against puncture upon needle withdrawal in the same manner described herein when applied to a biopsy needle. The biopsy specimen can then be removed in the safety of the lab by grabbing the sides of protector guard housing in a vice and slowly withdrawing the cannula. Thus, reference herein and in the claims to apparatus of the catheter type is intended to include all such applications. Further, it is intended to include all modifications and alterations to the device disclosed herein insofar as they come within the scope of the invention.

Having thus defined the invention, it is claimed:

1. Medical needle apparatus of the catheter type for preventing accidental puncture, said catheter type needle comprising:
   a smooth, hollow needle having a standard cutting edge at its proximal end for effecting a puncture, a handle portion at its distal end and a cylindrical body portion between its ends;
   a catheter having a proximal forward end initially adjacent said needle's cutting edge, a hub portion at its distal end and a generally cylindrical body portion therebetween, said catheter slidably receiving said needle's body portion; and
   a hollow protector guard housing initially positioned to longitudinally extend between said catheter's hub portion and said needle's handle portion and slidably receiving said needle's body portion, said guard housing having an open forward end initially engaged with said catheter's hub portion and a rearward end with a rearward opening initially adjacent said needle's handle portion; resilient spring means within said guard housing actuated upon movement of said cutting edge of said needle out of said catheter's hub portion to snap close said forward end opening of said guard housing and friction retention means in the form of friction material within said housing which, upon closing of said forward end opening, comes into contact with said needle, said spring means effective upon closing of said forward end opening to exert sufficient force between said friction material and said needle to retain said needle's cutting edge within said guard housing thereby preventing inadvertent puncture from said needle after use.

2. The apparatus of claim 1 wherein said guard housing has a hollow body portion extending between its forward and rearward ends, said body portion including a resilient sidewall segment formed therein extending from said forward end towards said rearward end, said sidewall segment including a closure wall terminating at a constant edge surface adjacent said guard housing's forward open end and sized to substantially cover said guard housing's forward open end, said closure wall's contact edge surface in contact with said needle's body portion when said needle is within said catheter to resiliently bias said sidewall segment outwardly from guard housing's body portion whereby said sidewall segment resiliently snaps said closure wall over said guard housing's open forward end when said needle's cutting edge is moved out of said catheter past said closure wall.

3. The apparatus of claim 2 wherein said friction retention means includes said friction material positioned on said inner surface of said longitudinal wall portion of said sidewall segment.

4. The apparatus of claim 2 wherein said guard housing's sidewall segment includes a longitudinal wall portion contiguous with and extending from said rearward end of said guard housing's body portion and terminating at said closure wall, said longitudinal wall portion having an outer surface and an inner surface with the distance therebetween defining the thickness of said sidewall segment's longitudinal wall portion, said thickness being varied whereby said sidewall segment can be resiliently stressed outwardly without fracture from said guard housing's body portion.

5. The apparatus of claim 4 wherein said guard housing having an inwardly-extending, rearward needle support defining said guard housing's rearward end as substantially closed with said rearward opening formed in said rearward end about said rearward support and through which said needle body portion extends whereby accidental puncture to the clinician from contact with said needle's cutting edge through said guard housing's rearward end is prevented.

6. The apparatus of claim 5 wherein said guard housing's body portion having an inwardly-extending forward needle support adjacent said guard housing's forward end and positioned away from and between said rearward needle support surface and said closure wall of said sidewall segment whereby said body portion of said needle is in sliding engagement with said rearward needle support, said forward needle support and said closure wall's contact edge surface.

7. The apparatus of claim 6 wherein said guard housing's body portion is recessed between said forward needle support surface and said rearward support needle surface and said friction retention means includes a friction material within said recess, said friction material having an exposed surface facing said needle's body portion, and extending inwardly within said guard housing's body portion a distance less than that distance which said forward and rearward needle supports extend whereby said needle's body portion becomes frictionally wedged against said exposed surface and said friction material only when said needle's cutting edge is pulled out of said catheter past said needle forward support.

8. The apparatus of claim 1 further including detent means formed in said hub portion of said catheter and said forward end of said guard housing for initially maintaining said guard housing connected to said catheter's hub portion while permitting separation of said guard housing from said hub portion upon actuation of said resilient spring means.

9. The apparatus of claim 8 wherein said resilient means engages said detent means to separate said catheter from said forward end of said guard housing when said resilient means is actuated.

10. The apparatus of claim 8 wherein said guard housing has a hollow body portion extending between its forward and rearward ends, said body portion including a resilient sidewall segment formed therein extending from said forward end towards said rearward end, said sidewall segment including a closure wall terminating at a contact edge surface adjacent said guard housing's forward open end and sized to substantially cover said guard housing's forward open end, said closure wall's contact edge surface in contact with said needle's body portion when said needle is within said catheter to resiliently bias said sidewall segment outwardly from guard housing's body portion whereby said sidewall segment resiliently snaps said closure wall over said guard housing's open forward end when said needle's cutting edge is pulled out of said catheter past said closure wall.

11. The apparatus of claim 10 wherein said detent means is effective to provide a hub-guard housing force for retaining said guard housing coupled to said hub portion of said catheter and said friction retention means is effective to provide a needle retention force retaining said needle within said guard housing, said needle retaining force being greater than hub-guard housing force whereby separation of said guard housing from said catheter is assured when said needle's cutting end is withdrawn from said catheter.

12. The apparatus of claim 11 where said resilient means engages said detent means to separate said catheter from said forward end of said guard housing when said resilient means is actuated.

13. The apparatus of claim 11 wherein said detent means includes diametrically opposed, radially-outwardly extending, conventionally-standard catheter locking ears on said catheter's hub portion and said forward end of said guard housing having a recessed notch formed therein for receiving said ears whereby said hub portion is initially engaged with said guard housing while said ears are pulled from said recess to separate said guard housing from said hub portion of said catheter upon needle withdrawal.

14. The apparatus of claim 10 further including said guard housing having an inwardly-extending, rearward needle support defining said guard housing's rearward end as substantially closed with said rearward opening formed in said rearward end about said rearward support and through which said needle body portion extends whereby accidental puncture to the clinician from contact with said needle's cutting edge through said guard housing's rearward end is prevented.

15. The apparatus of claim 14 further including said guard housing's body portion having an inwardly-extending forward needle support adjacent said guard housing's forward end and positioned away from and between said rearward needle support surface and said closure wall of said sidewall segment whereby said body portion of said needle is in sliding engagement with said rearward needle support, said forward needle support and said closure wall's contact edge surface.

16. The apparatus of claim 15 wherein said guard housing's body portion is recessed between said forward needle support surface and said rearward support needle surface and said friction retention means includes a friction material within said recess, said friction material having an exposed surface facing said needle's body portion, and extending inwardly within said guard housing's body portion a distance less than that distance which said forward and rearward needle supports extend whereby said needle's body portion becomes frictionally wedged against said exposed surface and said friction material only when said needle's cutting edge is pulled out of said catheter past said needle forward support so that said needle is free to pivot about said rear support and wedge itself into said friction material.

17. The apparatus of claim 16 wherein said guard housing's sidewall segment includes a longitudinal wall portion contiguous with and extending from said rearward and of said guard housing's body portion and terminating at said closure wall, said longitudinal wall portion having an outer surface and an inner surface with the distance therebetween defining the thickness of said sidewall segment's longitudinal wall portion, said thickness being reduced at said rearward end of said guard housing whereby said sidewall segment can be resiliently stressed outwardly without fracture from said guard housing's body portion.

18. The apparatus of claim 17 wherein said friction retention means includes said friction material positioned on said inner surface of said longitudinal wall portion of said sidewall segment.

19. Medical needle apparatus of the catheter type for preventing accidental puncture, said catheter type needle comprising:

a needle having a cutting edge at its proximal end for effecting a puncture, a handle portion at its distal end and a cylindrical body portion between its ends;

a catheter having a proximal forward end initially adjacent said needle's cutting edge, a hub portion at its distal end and a generally cylindrical body portion therebetween, said catheter slidably receiving said needle's body portion;

a hollow protector guard housing in between said catheter's hub portion and said needle's handle portion and slidably receiving said needle's body portion, said guard housing having an open forward end initially engaged with said catheter's hub portion and a rearward end with a rearward opening initially adjacent said needle's handle portion; resilient spring means within said guard housing actuated upon movement of said cutting edge of said needle out of said catheter to snap close said forward end opening of said guard housing and friction retention means within said housing effective upon actuation of said spring means to frictionally engage said needle and retain said needle's cutting edge within said guard housing thereby preventing inadvertent puncture from said needle after use;

detent means between said hub portion of said catheter and said forward end of said guard housing for initially maintaining said guard housing connected to said catheter's hub portion while permitting separation of said guard housing from said hub portion after actuation of said resilient spring means, said resilient means cooperating with said detent means to separate said catheter from said forward end of said guard housing when said resilient means is actuated;

said guard housing having a hollow body portion extending between its forward and rearward ends, said body portion including a resilient sidewall segment forward therein extending from said forward end towards said rearward end, said sidewall segment including a closure wall terminating at a contact edge surface adjacent said guard housing's forward open end and sized to substantially cover said guard housing's forward open end, said closure wall's contact edge surface in contact with said needle's body portion when said needle is within said catheter to resiliently bias said sidewall segment outwardly from guard housing's body portion; said sidewall segment further including a longitudinal wall portion contiguous with and extending from said rearward and of said guard housing's body portion and terminating at said closure wall, said longitudinal wall portion having an outer surface and an inner surface with the distance therebetween defining the thickness of said sidewall segment's longitudinal wall portion, said thickness being reduced at said rearward end of said guard housing, said guard housing further having an inwardly-extending, rearward needle support defining said guard housing's rearward end as substantially closed with said rearward opening formed in said rearward end about said rearward support and through which said needle body portion extends and an inwardly-extending forward needle support adjacent said guard housing's forward end and positioned away from and between said rearward needle support surface and said closure wall of said sidewall segment; said guard housing's body portion being recessed between said forward needle support surface and said rearward support needle surface and said friction retention means includes a friction material within said recess, said friction material having an exposed surface facing said needle's body portion and extending inwardly within said guard housing's body portion a distance less than that distance which said forward and rearward needle supports extend, said friction retention means also including said friction material positioned on said inner surface of said longitudinal wall portion of said sidewall segment; and said friction generating material in said recess is formed with a V shaped groove in its exposed surface for restingly receiving said needle body portion when said needle's cutting edge is withdrawn from said catheter.

20. In an intravenous catheter type apparatus having a smooth, hollow needle with a handle and a standard cutting edge at its proximal end for effecting a puncture at a site on a patient and a catheter with a hub portion initially adjacent said handle which is to be left at the puncture site for intravenous feeding and like applications after said needle is removed, the improvement comprising:

a hollow protector guard housing initially positioned to longitudinally extend between said catheter's hub portion and said needle's handle portion and slidably receiving said needle's body portion, said guard housing having an open forward end initially engaged with said catheter's hub portion and a rearward end with a rearward opening initially adjacent said needle's handle portion; resilient spring means within said guard housing actuated upon movement of said cutting edge of said needle out of said catheter's hub portion to exert its spring bias to snap close said forward end opening of said guard housing and friction retention means in the form of friction material situated within said housing initially out of contact with said needle and in contact with said needle upon closure of said forward end opening, said spring means also effective to develop sufficient contact force between said needle edge and said friction material to prevent said needle edge from leaving said guard housing thereby preventing inadvertent puncture from said needle after use.

21. The apparatus of claim 20 wherein said guard housing has a hollow body portion extending between its forward and rearward ends, said body portion including a resilient sidewall segment formed therein extending from said forward end towards said rearward end, said sidewall segment including a closure wall terminating at a contact edge surface adjacent said guard housing's forward open end and sized to substantially cover said guard housing's forward open end, closure wall's contact edge surface in contact with said needle's body portion when said needle is within said catheter to resiliently bias said sidewall segment outwardly from said guard housing's body portion whereby said sidewall segment resiliently snaps said closure wall over said guard housing's open forward end when said needle's cutting edge is pulled out of said catheter past said closure wall.

22. The apparatus of claim 21 wherein said rearward end of said guard housing defines a rearward needle support extending from said body portion to said rearward opening in said guard housing's rearward end, said guard housing's body portion having an inwardly-extending forward needle support adjacent said guard housing's forward end and positioned away from and between said rearward needle support and said closure wall of said sidewall segment whereby said body portion of said needle is in sliding engagement with said rearward needle support, said forward needle support and said closure wall's contact edge surface.

23. The apparatus of claim 22 wherein said guard housing's body portion is recessed between said forward needle support and said rearward needle support and said friction retention means includes a friction material within said recess, said friction material having an exposed surface adjacent said needle's body portion, said exposed surface extending inwardly within said guard housing's body portion a distance less than that distance which said forward and rearward needle support extend whereby said needle's body portion becomes frictionally wedged against said exposed surface only when said needle's cutting edge is pulled out of said catheter past said needle forward support surface.

24. The apparatus of claim 20 further including detent means formed in said hub portion of said catheter and said forward end of said guard housing for initially maintaining said guard housing connected to said catheter's hub portion while permitting separation of said guard housing from said hub portion after actuation of said resilient spring means.

25. The apparatus of claim 24 wherein said detent means includes said catheter's hub portion having diametrically opposed, radially-outwardly extending, conventionally-standard catheter locking ears and said forward end of said guard housing having a recessed notch formed therein for receiving said ears whereby said hub portion is engaged with said guard housing.

26. The apparatus of claim 24 wherein said detent means is effective to provide a hub-guard housing force for retaining said guard housing connected to said hub portion of said catheter and said friction retention means is effective to provide a needle retention force retaining said needle within said guard housing, said needle retaining force being greater than said hub-guard housing force whereby separation of said guard housing from said catheter is assured when said needle's cutting end is withdrawn from said catheter's hub portion.

27. The apparatus of claim 26 wherein said resilient means engages said detent means to separate said catheter from said forward end of said guard housing when said resilient means is actuated.

28. The apparatus of claim 26 wherein said detent means includes said catheter's hub portion having diametrically opposed, radially-outwardly extending, conventionally-standard catheter locking ears and said forward end of said guard housing having a recessed notch formed therein for receiving said ears whereby said hub portion is engaged with said guard housing.

29. The apparatus of claim 24 wherein said guard housing has a hollow body portion extending between its forward and rearward ends, said body portion including a resilient sidewall segment formed therein extending from said forward end towards said rearward end, said sidewall segment including a closure wall terminating at a contact edge surface adjacent said guard housing's forward open end and sized to substantially cover said guard housing's forward open end, said closure wall's contact edge surface in contact with said needle's body portion when said needle is within said catheter to resiliently bias said sidewall segment outwardly from guard housing's body portion whereby said sidewall segment resiliently snaps said closure wall over said guard housing's open forward end when said needle's cutting edge is pulled out of said catheter past said closure wall.

30. The apparatus of claim 29 wherein said rearward end of said guard housing defines a rearward needle support extending from said body portion to said rearward opening in said guard housing's rearward end, said guard housing's body portion having an inwardly-extending forward needle support adjacent said guard housing's forward end and positioned away from and between said rearward needle support and said closure wall of said sidewall segment whereby said body portion of said needle is in sliding engagement with said rearward needle support, said forward needle support and said closure wall's contact edge surface.

31. The apparatus of claim 30 wherein said guard housing's body portion is recessed between said forward needle support and said rearward needle support and said friction retention means includes a friction material within said recess, said friction material having an exposed surface adjacent said needle's body portion, said exposed surface extending inwardly within said guard housing's body portion a distance less than that distance which said forward and rearward needle support extend whereby said needle's body portion becomes frictionally wedged against said exposed surface only when said needle's cutting edge is pulled out of said catheter past said needle forward support surface so that said needle is free to pivot about said rear support and wedge itself, by said bias of said closure wall, into said friction material.

32. The apparatus of claim 31 wherein said guard housing's sidewall segment includes a longitudinal wall portion extending from said rearward end of said guard housing's body portion and terminating at said closure wall, said longitudinal wall portion having an outer surface and an inner surface with the distance therebetween defining the thickness of said sidewall segment's longitudinal wall portion, said thickness being varied whereby said sidewall segment can be resiliently stressed outwardly without fracture from said guard housing's body portion.

* * * * *